United States Patent
Vitali et al.

(10) Patent No.: US 7,409,241 B2
(45) Date of Patent: Aug. 5, 2008

(54) MONITORING THE SYMPATHICO-VAGAL ACTIVITY BY ANALYSIS OF ENDOCARDIAC ACCELERATION IN AN ACTIVE IMPLANTABLE MEDICAL DEVICE

(75) Inventors: Luca Vitali, Strambino (IT); Guido Gaggini, Milan (IT)

(73) Assignee: ELA Medical S.A.S., Montrouge (FR)

( * ) Notice: Subject to any disclaimer, the term of this patent is extended or adjusted under 35 U.S.C. 154(b) by 224 days.

(21) Appl. No.: 10/995,591

(22) Filed: Nov. 22, 2004

(65) Prior Publication Data
US 2005/0131470 A1 Jun. 16, 2005

(30) Foreign Application Priority Data
Nov. 21, 2003 (FR) .................................. 03 13629

(51) Int. Cl.
*A61B 5/02* (2006.01)
(52) U.S. Cl. .................. 600/513; 600/508; 600/509; 600/527; 607/9; 607/17; 607/19; 607/23; 607/44
(58) Field of Classification Search .............. 607/9, 607/17, 19, 23, 44; 600/527, 508–509, 513
See application file for complete search history.

(56) References Cited

U.S. PATENT DOCUMENTS 5,609,612 A * 3/1997 Plicchi et al. ............... 607/17
6,788,970 B1 * 9/2004 Park et al. ................... 607/17

FOREIGN PATENT DOCUMENTS

| EP | 0 515 319 A2 | 5/1992 |
| EP | 0 565 909 A2 | 3/1993 |
| EP | 0 655 260 A2 | 10/1994 |

OTHER PUBLICATIONS

G. Plicchi et al. "PEA I and PEA II based implantable haemodynamic monitor: pre clinical studies in sheep." Mar. 2, 2001, Europace (2002) 4, 49-54.*

* cited by examiner

*Primary Examiner*—Carl H. Layno
*Assistant Examiner*—Deborah Malamud
(74) *Attorney, Agent, or Firm*—Orrick Herrington & Sutcliffe, LLP

(57) ABSTRACT

An active implantable medical device having a function for monitoring the sympathico-vagal activity by an analysis of endocardiac acceleration. The device collects at least one physiological parameter of the patient, analyzes that collected parameter and delivers at an output data representative of the sympathico-vagal activity of the patient. The physiological parameter is an endocardiac acceleration (EA), and the representative data include at least one value function of the endocardiac acceleration, in particular a function of a first peak (PEA I) at the time of the phase of isovolumic ventricular contraction and/or of a second peak (PEA II) at the time of the phase of isovolumic ventricular relieving.

11 Claims, 3 Drawing Sheets

FIG_1

MONITORING THE SYMPATHICO-VAGAL ACTIVITY BY ANALYSIS OF ENDOCARDIAC ACCELERATION IN AN ACTIVE IMPLANTABLE MEDICAL DEVICE

FIELD OF THE INVENTION

The present invention relates to "active implantable medical devices" as defined by the Jun. 20, 1990 directive 90/385/CEE of the Council of the European Communities, more particularly to cardiac devices such as pacemakers, defibrillators and/or cardiovertors that are able to deliver to the heart low energy stimulation pulses for the treatment of the disorders of the cardiac rhythm. The invention relates to those devices that are equipped with a function for monitoring of the sympathico-vagal activity of the patient carrying the implanted apparatus.

BACKGROUND OF THE INVENTION

EP-A-0 565 909 (issued to Sorin Biomedica Cardio SpA) describes a device in which the sympathico-vagal activity is analyzed based upon the cardiac signal collected (sensed) by endocavitary electrodes, in particular by an analysis of the variability of RR intervals (intervals separating two consecutive spontaneous ventricular depolarizations). Interest in monitoring the sympathico-vagal activity arises from the possibility of predicting the imminent occurrence of a syncope of vaso-vagal origin, and preventing its occurrence by an adapted therapy, typically (but not exclusively) an antibradycardiac stimulation therapy.

Primarily, a syncope is a temporary loss of consciousness with a fall in the muscular tone, resulting from the temporary reduction of cerebral circulation. Among various types of syncopes, the vaso-vagal syncope is caused by a temporary imbalance of the regulation system of the vaso-vagal balance. This leads to an excessive activation of the vagal system, in turn resulting in a vasodilatation and a bradycardia leading to the syncope. One can anticipate syncope by a certain number of precursory signs. It is desirable among patients carrying a cardiac pacemaker to detect a risk of imminent occurrence of such a syncope and to apply a suitable therapy and to avoid the fainting of the patient.

It is generally considered that the vaso-vagal syncope comes from a state where the sympathetic nerve system has a particularly high reactivity that initiates an antagonistic response of the parasympathetic system, causing in turn a vasodilatation inducing a reduction of the filling of the ventricles and the bradycardia. Because the chain of events leading to the syncope begins several minutes before the loss of consciousness occurs, it is desirable to be able to detect such a state as soon as possible to be able to take the suitable required measures.

It is, however, unfortunately not possible to directly measure the balance of the autonomous nervous system. It is only possible to evaluate this state in an indirect manner based upon various physiological parameters such as the heartbeat rate, the myocardial contractility, the ventilatory activity or other parameters, or a combination of these various parameters. The known techniques, however, appear difficult to implement, taking into account in particular the multiplicity of the factors likely to modify the heartbeat rate, factors which are not necessarily related to an imbalance of the sympathico-vagal system.

The present invention has as an objective proposing an alternative approach to the analysis of the sympathico-vagal activity by an implanted device, while proposing to implement a detection based on the analysis of endocardiac acceleration, more particularly an analysis of the peaks of endocardiac acceleration.

One can collect (i.e., detect or sense) an endocardiac acceleration signal, as described in EP-A-0 515 319 (assigned to Sorin Biomedica Cardio SpA), which describes a endocavitary probe equipped with a distal stimulation electrode located at the bottom of the ventricle, and a micro-accelerometer able to measure the endocardiac acceleration. The endocardiac acceleration signal thus measured during a cardiac cycle forms, inter alia, two peaks corresponding to the two major noises that it is possible to recognize in each cycle of a healthy heart.

EP-A-0 655 260 (Sorin Biomedica Cardio SpA) describes a manner of processing the endocavitary acceleration signal delivered by the sensor located in the extremity of a probe to derive from it, in particular, the two peak values of endocardiac acceleration, useful in particular for the detection of cardiac disorders and the release (or not) of a therapy, for example, an antibradycardiac stimulation therapy accelerating the stimulation rate. The first peak of endocardiac acceleration ("PEA I") corresponds to the closing of the mitral and tricuspid valves, at the beginning of the isovolumic phase of ventricular contraction (i.e., the systole). The variations of this first peak are closely related to the variations of the pressure in the ventricle (the amplitude of peak PEA I, more precisely, being correlated to the positive maximum of the pressure variation dP/dt in the left ventricle) and can thus constitute a parameter representative of the contractility of the myocardium, itself related to the level of activity of the sympathetic nerve system. The second peak of endocardiac acceleration ("PEA II") corresponds to the closing of the aortic and pulmonary valves, at the moment of the isovolumic ventricular relaxation phase. This second peak, which is produced by the abrupt deceleration of the blood mass moving in the aorta, constitutes a parameter representative of the peripheral blood pressure at the beginning of the diastole.

The invention proposes to use this information for heretofore unknown and different purposes, namely, to analyze the sympathico-vagal activity of the patient.

OBJECTS AND SUMMARY OF THE INVENTION

The present invention is broadly directed to an active implantable medical device, in particular a cardiac pacemaker, defibrillator, cardiovertor and/or multisite device, or even an active implant with purely diagnostic feature, including means for collecting at least one physiological parameter of the patient, and means for analysing the collected physiological parameter and delivering at an output a data representative of the sympathico-vagal activity of the patient. In a manner characteristic of the present invention, the physiological parameter is an endocardiac acceleration and the aforementioned representative data include at least a value function of the endocardiac acceleration collected during a given cycle.

Preferably, the representative data include at least a value function of a peak of endocardiac acceleration, in particular a function of the values of the one and/or other of the aforementioned two peaks of endocardiac acceleration during a given cycle, namely a first peak at the time of the phase of isovolumic ventricular contraction and a second peak at the time of the phase of isovolumic ventricular relaxation.

The aforementioned representative data can be related to an average of the values of peaks of endocardiac acceleration collected during a plurality of successive cycles, or a variation of the values of peaks of endocardiac acceleration collected during a plurality of consecutive cycles, or of a difference between a long-term average and a short-term average of the values of the peaks of endocardiac acceleration collected during a plurality of successive cycles.

Preferably, the device further includes means for detecting a risk of a syncope, receiving at an input the aforementioned given representative data and delivering at an output an alarm signal in the event of proven risk of imminent occurrence of a syncope.

It is thus possible to control a means for applying a preventive therapy, operative in response to the delivery of an alarm signal, by modification of an operating parameter and/or a release of a therapeutic function of the device, e.g., an increased or accelerated stimulation rate.

The means for detecting can include means for comparing the aforementioned representative data with a predetermined threshold and to produce an alarm signal in response to the data crossing of this threshold. Alternately, the means for comparing can include a 'state machine' able to compare the aforementioned representative data with a plurality of predetermined thresholds, to detect the crossing(s) of the various thresholds, to analyze the sequence of such crossings, and to produce an alarm signal on detection of one or more predetermined sequences of crossings. In yet another alternative, the means for comparing can be a means for applying an autocorrelation process of a morphological analysis, a frequential analysis, and/or an analysis by wavelets, of the physiological parameter indicative of endocardiac acceleration.

The representative data can include: a long-term average and a short-term average of the values of the first and second peaks of endocardiac acceleration collected during a plurality of successive cycles, and a long-term average and a short-term average of heart rate values. They can also include a value function of the heart rate of the patient. The means for detecting can also include means for producing an alarm signal when, by a selected factor of proportionality:

(1) the short-term average of the values of the second peaks of acceleration is lower than the long-term average of the values of the second peaks of acceleration and the short-term average of the values of heart rate is higher than the long-term average of the values of heart rate, for a given percentage of cycles over a predetermined number of successive cycles, or (2) the short-term average of the values of the first peaks of acceleration is lower than the long-term average of the values of the first peaks of acceleration and the short-term average of the values of heart rate is higher than the long-term average of the values of heart rate, for a given percentage of cycles over a predetermined number of successive cycles.

DETAILED DESCRIPTION OF THE INVENTION

One will now describe a realization of the device of the invention, which can be implemented by suitable programming of the control software of a known active implantable medical device equipped with a function for monitoring of the sympathico-vagal activity of the patient carrying the implanted apparatus. Such devices include pacemakers, defibrillators and/or cardiovertors that are able to deliver to the heart low energy stimulation pulses for the treatment of disorders of the cardiac rhythm.

Suitable devices for which the present invention has application include, for example, the active implantable medical devices available from ELA Médical, Montrouge, France. These devices are microprocessor-based systems having circuits for receiving, conditioning, and processing detected electrical signals, and are capable of receiving software instructions by telemetry, storing them in memory, and then executing those instructions to perform the functions described above in implementing the present invention.

Figure 2:
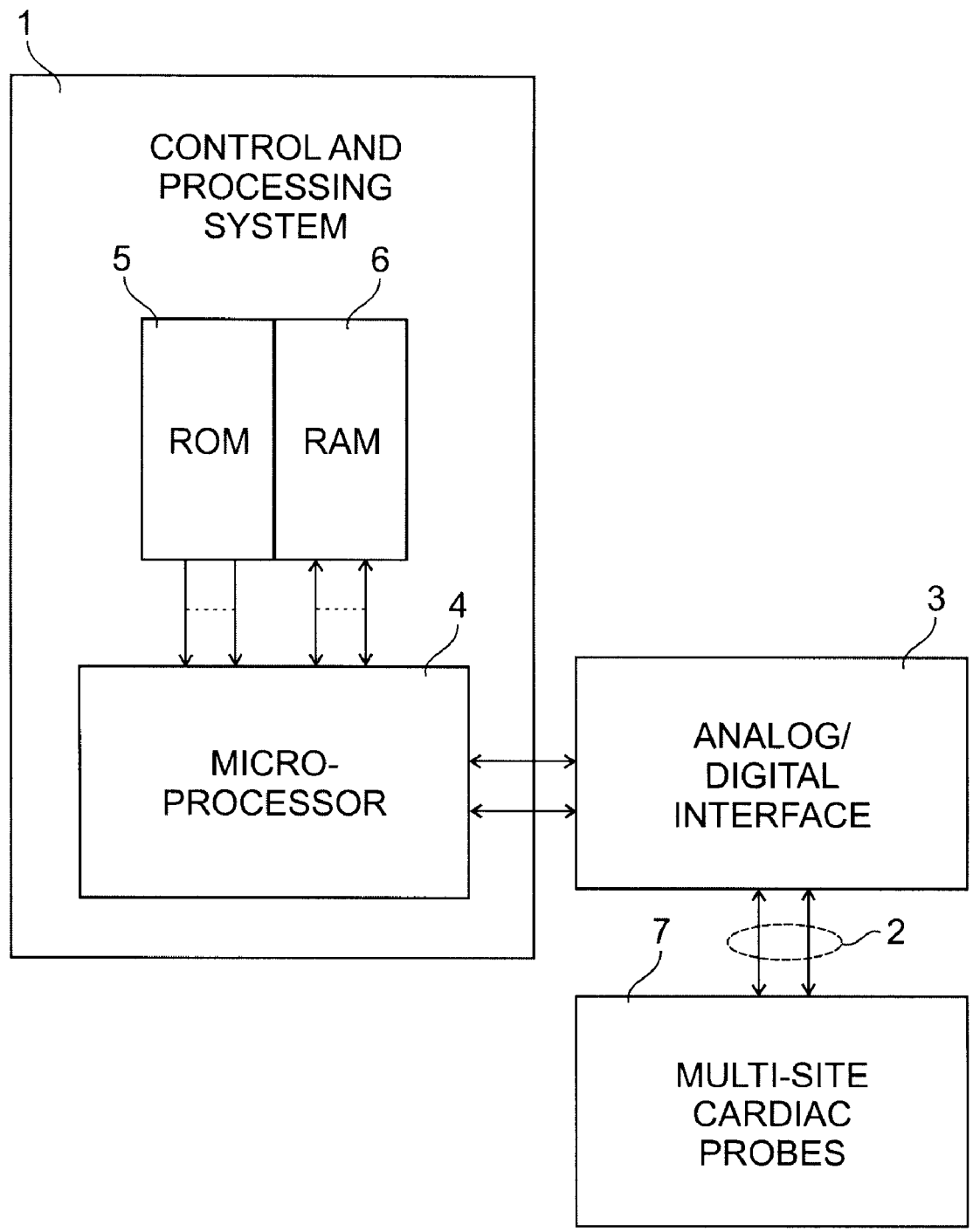
FIG. 2 illustrates schematically the general use of a device according to the invention.

FIG. 2 illustrates in block form the typical structure of an implantable medical device of this type, including a control and processing system 1, multiple leads 2 connected to probes at cardiac sites, an analog/digital interface for transferring the analog signals from the leads 2 to the micro-processor 4 and vice versa, a micro-processor 4 for the processing of instructions necessary in implementing the algorithm of the present invention, ROM 5 and RAM 6 for storing the software instructions and data for implementing the algorithm of the present invention, and cardiac probes 7 placed at multiple cardiac sites as is typical of known multi-site pacemakers. The creation of suitable software instructions for controlling an implant to perform the aforementioned functions of the present invention are within the abilities of a person of ordinary skill in the art. The detection circuits used to detect the cardiac signals in the atrium and the ventricle and the endocardial accelerations signal, in the left and/or right chambers, are well known and any suitable design may be used.

Figure 1:
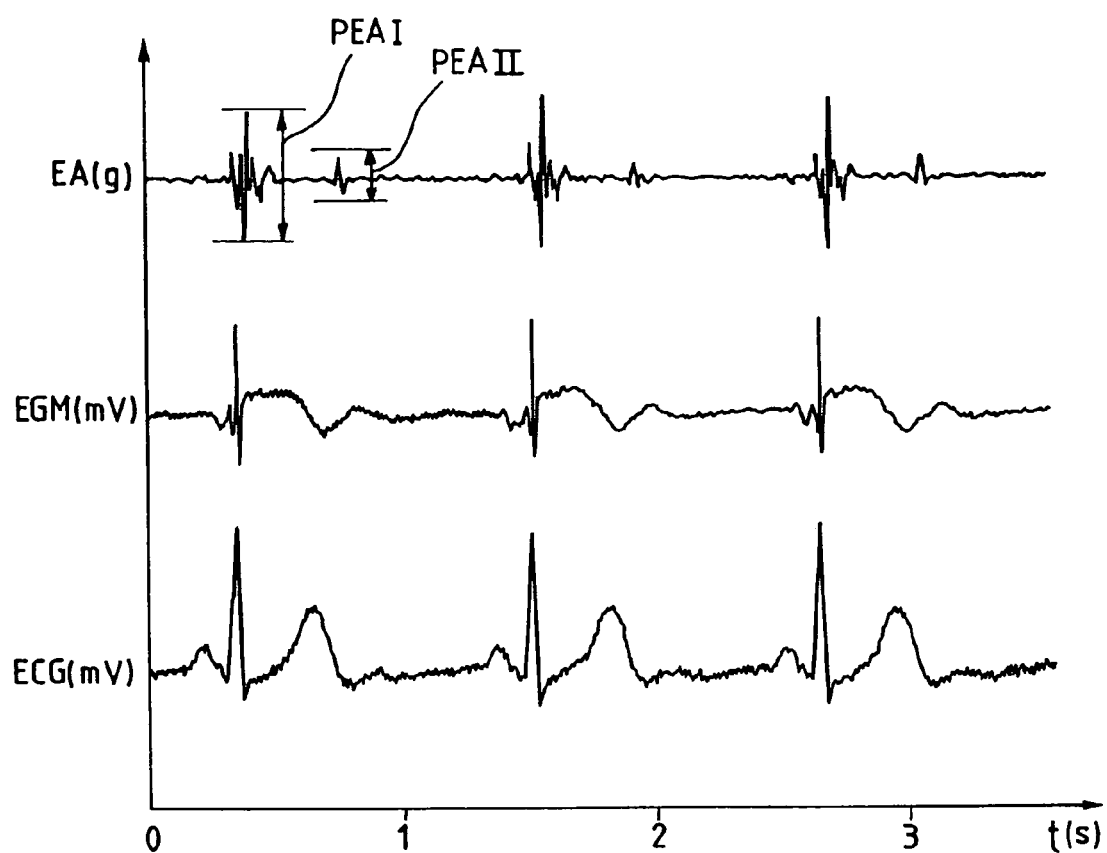
FIG. 1 is a chronogram showing the variations of endocavitary acceleration, as well as corresponding electrogram and surface electrocardiogram, during three successive cardiac cycles.

In FIG. 1, the top curve is an illustration of a signal indicative of the variations of the endocardiac acceleration (EA), collected by a sensor such as that described in the above-mentioned EP-A-0 515 319, integrated into an endocavitary probe head placed in the bottom (i.e., at the base) of the ventricle. Also illustrated in FIG. 1 are the layouts of electrogram (EGM), i.e., the electric signal collected by the distal electrode of this same probe, and a corresponding surface electrocardiogram (ECG), during three consecutive cardiac cycles.

As explained above, the endocardiac acceleration presents two successive peaks, whose amplitude can be determined by a suitable processing of the signal delivered by the acceleration sensor, as described in EP-A-0 655 260 above mentioned. It should be understood that "peak" refers to the maximum value peak-to-peak of the signal of acceleration separating both extrema, positive and negative, corresponding to variations PEA I and PEA II indicated on the chronogram of FIG. 1.

These values of peaks PEA I and/or PEA II are recorded during successive cycles and are analyzed to detect a situation of the risk of an imminent occurrence of a vaso-vagal syncope. One will note that the analysis can only be applied to signal PEA I alone, to the signal PEA II alone, or to a combination of two signals PEA I and PEA II. Parameter(s) PEA I and/or PEA II can be treated in various ways.

A first technique is determining, cycle to cycle, the absolute values that these parameters can take and to fix the thresholds for the release of an alarm, or preferably to determine an averaged value of these parameters over a predetermined number of cycles, to avoid the influences of the cycle-to-cycle variability (dispersion of measurements) and the non-significant short events.

To improve the specificity of the detection, and in particular to take account of the differences in the basic value of the PEA parameters from one patient to the next, it can be advantageous to analyze the variations of these parameters, rather than their absolute values.

A manner of proceeding concerns analyzing the difference between a short-term average and a long-term average of the same parameter. If this parameter varies little, the difference will be low and the two values will end up coinciding. On the other hand, as soon as the parameter becomes unstable, the short-term average will follow the variations of the parameter more quickly than the long-term average. The difference between the two averages will no longer be null or quasi-null, but will take a positive value (in the event of an increase in the parameter) or a negative value (in the event of a reduction), the absolute value of this variation depends on the analyzed parameter and its speed of variation.

To decide about the presence or absence of an imminent risk of syncope, one or more thresholds are fixed, and each PEA I or PEA II parameter (or a combination of the two parameters), is compared with a predetermined threshold. The result of the comparison can be combined in various ways with the result of similar comparisons of other parameters to produce an output signal having two states, one state associated with a normal situation and the other state associated with an alarm of risk of syncope. One will give in the example below the details of implementation of such a technique.

It is also possible to use a "state machine", where the results of the comparisons to various thresholds are applied to a state transition system, and a memory, such that the decision to start an alarm of risk of syncope according to a diagram of a more complex evolution.

Other types of analyses, more complex, also can be implemented to improve further the quality of the process of detection, for example, through the techniques of correlation by an analysis of morphology of the signal, a frequential analysis, an analysis by wavelets, etc.

The process of detection can also take into account not only parameters PEA I and/or PEA II, but also other parameters such as the heart rate, or signals delivered by an activity sensor, e.g., a ventilation-minute sensor, etc.

The system can also be self-adapting, i.e., it can adapt to variations over the long term or that it can determine whether, after having produced a syncope alarm signal, a syncope actually occurs or not, in order to improve later the specificity of the detection system.

EXAMPLE

Figure 3:
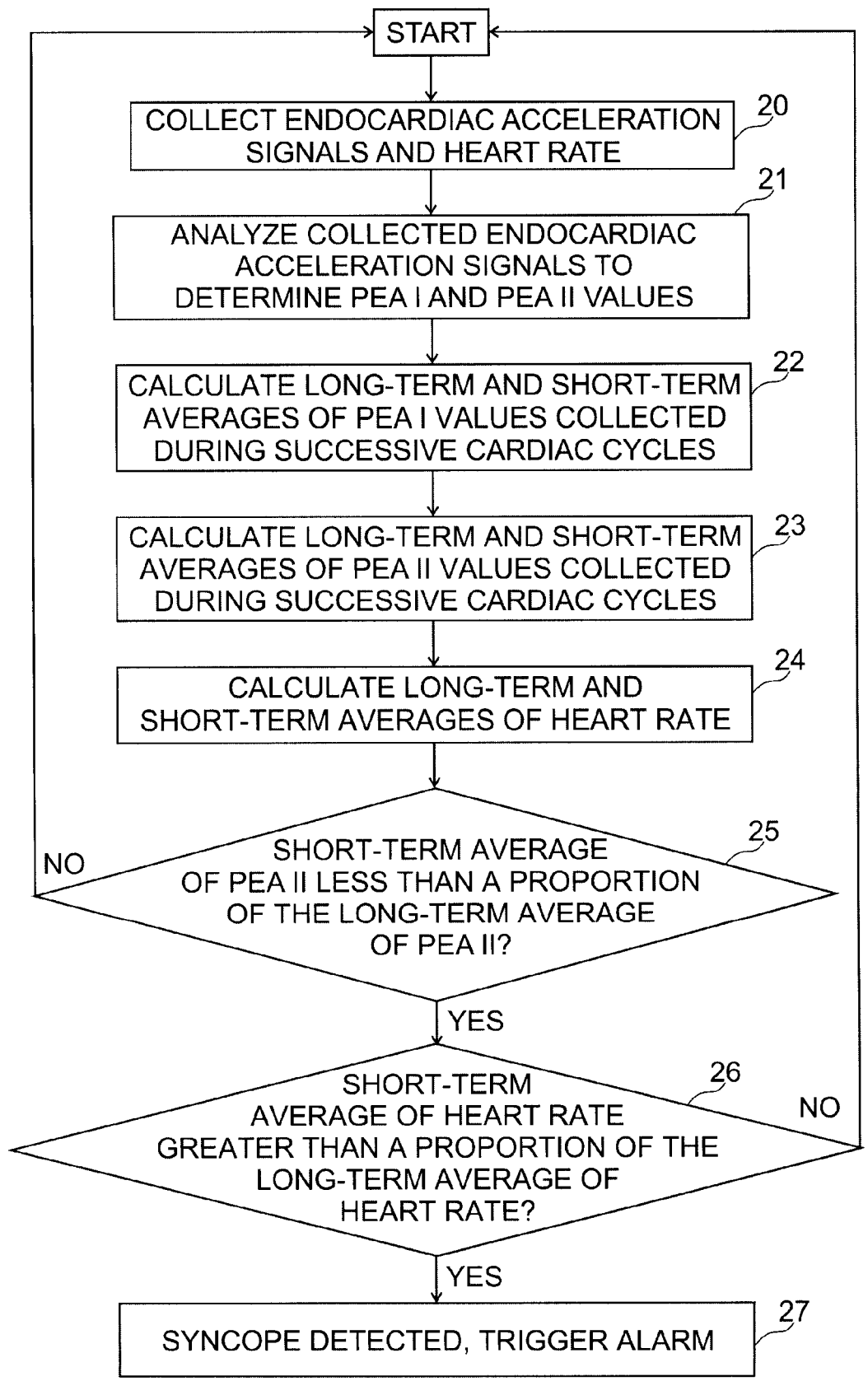
FIG. 3 illustrates a flow chart implementing an algorithm for monitoring the sympathico-vagal activity by analysis of endocardiac acceleration in an active implantable medical device according to the invention

One now will describe an example of a detection algorithm based on the combined analysis of the first peak of acceleration (PEA I), of the second peak of acceleration (PEA II), and of the heart rate, with reference to the flow chart of FIG. 3. In stages 20, 21, 22, 23, and 24 of FIG. 3, these three quantities are measured with each cardiac cycle and an algorithm calculates, for each one of them, two sliding averages; a long-term average and short-term average, these averages being updated regularly (e.g., each cycle, every four cycles, every ten cycles, etc).

The algorithm determines the six following quantities:
$PEA1_{LT}$: long term sliding average (for example, over 1000 cycles) of PEA I parameter,
$PEA1_{ST}$: short term sliding average (for example, over 30 cycles) of PEA I parameter,
$PEA2_{LT}$ long term sliding average (for example, over 1000 cycles) of PEA II parameter,
$PEA2_{ST}$: short term sliding average (for example, over 30 cycles) of PEA II parameter,
$FC_{LT}$: in long term sliding average (for example, over 5000 cycles) of the heart rate,
$FC_{ST}$: short term sliding average (for example, over 100 cycles) of the heart rate.

To determine the risk of occurrence of a syncope, the algorithm evaluates the three following Boolean quantities.

$$(PEA2_{ST} < k_1 \cdot PEA2_{LT}) \ \& \ (FC_{ST} > k_2 \cdot FC_{LT}) \quad (1)$$

$$(PEA1_{ST} < k_3 \cdot PEA1_{LT}) \ \& \ (FC_{ST} > k_4 \cdot FC_{LT}) \quad (2)$$

$$(PEA2_{ST} < k_5 \cdot PEA2_{LT}) \ \& \ (FC_{ST} > k_6 \cdot FC_{LT}) \quad (3)$$

If condition (1) is fulfilled, it indicates that although the heart rate increases above its basic value, the PEA II parameter decreases. This represents a peripheral diastolic blood pressure decrease, corresponding to an abnormal situation. An alarm is thus triggered on the satisfaction of this condition.

If condition (2) is fulfilled, it indicates that although the heart rate increases above the basic value, the PEA I parameter decreases. This represents a decrease in myocardic contractility, revealing a decline in the activity of the sympathetic system, a situation here still considered to be abnormal. An alarm is thus triggered on the satisfaction of this condition.

Condition (3) corresponds to condition (1) but with more strict criteria. If it is satisfied, as shown in stages 25 and 26 of FIG. 3, it reveals a state relatively close to the syncope, in which the autonomous nervous system is no longer able to control the stability of the blood pressure. As shown in stage 27 of FIG. 3, an alarm is thus triggered on the satisfaction of this condition.

An example of application numerical for the factors $k_1$ to $k_6$ is:

$$(PEA2_{ST} < 0.75 \cdot PEA2_{LT}) \ \& \ (FC_{ST} > 1.25 \cdot FC_{LT}) \quad (1)$$

$$(PEA1_{ST} < 0.95 \cdot PEA1_{LT}) \ \& \ (FC_{ST} > 1.25 \cdot FC_{LT}) \quad (2)$$

$$(PEA2_{ST} < 0.55 \cdot PEA2_{LT}) \ \& \ (FC_{ST} > FC_{LT}) \quad (3)$$

Various implementations can be considered in alternative or complement to the mode of analysis given in the example above. It is in particular possible to evaluate the risk of occurrence of a syncope based upon an analysis of the energy contained in the peak PEA I and/or peak PEA II endocardiac acceleration signal, or by an analysis of the endocardiac acceleration signal, such as a time frequency analysis or an analysis of the area under the curve of the signal, or an analysis of the width of the peak.

One skilled in the art will appreciate that the present invention can be practiced by other than the described embodiments, which are presented for purposes of illustration and not of limitation.

We claim:

1. An active implantable medical device, including:
   means for collecting an endocardiac acceleration parameter of a patient;
   means for analyzing said collected endocardiac acceleration signal including means for determining a first peak endocardiac acceleration (PEA I) corresponding to a phase of isovolumic ventricular contraction in a given cardiac cycle and a second peak endocardiac acceleration (PEA II) corresponding to a phase of isovolumic ventricular relaxation in said given cardiac cycle, and means for determining a heart rate of a patient;

means for calculating a long-term average and a short-term average of the values of the first peaks of endocardiac acceleration (PEA I) collected at the time of the phase of isovolumic ventricular contraction during a plurality of successive cycles;

means for calculating a long-term average and a short-term average of the values of the second peaks of endocardiac acceleration (PEA II) collected at the time of the phase of isovolumic ventricular contraction collected during a plurality of successive cycles;

means for calculating a long-term average and a short-term average of the values of heart rate;

means for delivering at an output a data representative of sympathico-vagal activity of the patient, wherein said data representative of sympathico-vagal activity comprises said calculated long-term and short-term averages of said first peak, second peak, and heart rate; and means for detecting a risk of syncope when the short-term average of the values of the second peaks of endocardiac acceleration (PEA II) is less than the long-term average of the values of the second peaks of endocardiac acceleration (PEA II) and the short-term average of the values of heart rate is greater than the long-term average of the values of heart rate.

2. The device of claim 1, further comprising means for delivering at an output an alarm signal in response to a detected risk of imminent occurrence of a syncope.

3. The device of claim 2, further comprising means for delivering a therapy in response to a delivered alarm signal.

4. The device of claim 3 wherein said therapy delivering means further comprises means for modifying an operating parameter of said device.

5. The device of claim 3 wherein said therapy delivering means further comprises means for releasing a therapeutic function of said device.

6. The device of claim 2, wherein the detecting means further comprises means for comparing said representative data with a predetermined threshold and producing said alarm signal at a crossing of said threshold.

7. The device of claim 2, wherein said detecting means further comprises a state machine able to compare said representative data with a plurality of predetermined thresholds, and means for detecting crossings of said thresholds, analyzing a sequence of said crossings, and producing an alarm signal in response to said sequence of crossings corresponding to a preselected crossing sequence.

8. The device of claim 2, wherein said analysing means further comprises means for applying to the detected endocardiac acceleration physiological parameter an autocorrelation process selected from among the group consisting of a morphological analysis, a frequential analysis, and a wavelets analysis.

9. The device of claim 2, wherein the means for detecting further comprises means for producing an alarm signal when, by a factor of proportionality, the short-term average of the values of the second peaks of acceleration is lower than the long-term average of the values of the second peaks of acceleration and the short-term average of the values of heart rate is higher than the long-term average of the values of heart rate, for a given percentage of cycles over a predetermined number of successive cycles.

10. The device of claim 2, wherein the means for detecting further comprises means for producing an alarm signal when, by a factor of proportionality, the short-term average of the values of the first peaks of acceleration is lower than the long-term average of the values of the first peaks of acceleration and the short-term average of the values of heart rate is higher than the long-term average of the values of heart rate, for a percentage given of cycles over a predetermined number of successive cycles.

11. An active implantable medical device comprising a computer readable medium encoded with one or more computer programs performing the steps of:

collecting an endocardiac acceleration parameter of a patient;

analyzing said collected endocardiac acceleration signal including determining a first peak endocardiac acceleration (PEA I) corresponding to a phase of isovolumic ventricular contraction in a given cardiac cycle and a second peak endocardiac acceleration (PEA II) corresponding to a phase of isovolumic ventricular relaxation in said given cardiac cycle, and determining a heart rate of a patient;

calculating a long-term average and a short-term average of the values of the first peaks of endocardiac acceleration (PEA I) collected at the time of the phase of isovolumic ventricular contraction during a plurality of successive cycles;

calculating a long-term average and a short-term average of the values of the second peaks of endocardiac acceleration (PEA II) collected at the time of the phase of isovolumic ventricular contraction collected during a plurality of successive cycles;

calculating a long-term average and a short-term average of the values of heart rate;

delivering at an output a data representative of sympathico-vagal activity of the patient, wherein said data representative of sympathico-vagal activity comprises said calculated long-term and short-term averages of said first peak, second peak, and heart rate; and detecting a risk of syncope when the short-term average of the values of the second peaks of endocardiac acceleration (PEA II) is less than the long-term average of the values of the second peaks of endocardiac acceleration (PEA II) and the short-term average of the values of heart rate is greater than the long-term average of the values of heart rate.

* * * * *